United States Patent [19]

Fruchey

[11] Patent Number: 4,980,496

[45] Date of Patent: Dec. 25, 1990

[54] METHOD FOR PRODUCING $C_1$ TO $C_5$ ALKYL NITRIDES

[76] Inventor: Olan S. Fruchey, 2310 Raintree, Corpus Christi, Tex. 78409

[21] Appl. No.: 446,028

[22] Filed: Dec. 5, 1989

[51] Int. Cl.$^5$ .......................................... C07C 201/08
[52] U.S. Cl. ................................................... 558/488
[58] Field of Search ........................................ 558/488

[56] References Cited

U.S. PATENT DOCUMENTS

| | | | |
|---|---|---|---|
| 2,166,698 | 7/1939 | Allen | 558/488 |
| 2,465,984 | 5/1946 | Doumani et al. | 558/488 |
| 2,739,166 | 3/1956 | Treacy | 558/488 |
| 2,831,882 | 4/1958 | Spaeth | 558/488 |
| 3,214,458 | 10/1965 | De Rooij et al. | 558/488 |
| 4,353,843 | 10/1982 | Doumaux, Jr. et al. | 260/466 |
| 4,908,466 | 3/1990 | Nelson | 558/488 |

OTHER PUBLICATIONS

Organic Synthesis Collection; vol. 2, 108 (1943), N-Butyl Nitrite.
Organic Synthesis Collection; vol. 3, 191 (1955), Omega-Chloronitrosoacetophenone.
Chemical Abstracts, 1964, No. 4090, Nitrites.
Chemical Abstracts, 1958, No. 15565, Nitrite Esters.
Chemical Abstracts, 1944, No. 5809, Omega—Chloroisonitrosoacetophenone.
Chemical Abstracts, vol. 30, No. 811, Isopropyl Nitrite.
Chemical Abstracts CA110(17): 153420b.
Chemical Abstracts CA100(17): 138331y.
Chemical Abstracts CA 98(11): 88649a.
Chemical Abstracts CA90(8): 64324z.
Chemical Abstracts CA89(4): 26345d.
Chemical Abstracts CA88(4) 24132n.
Chemical Abstracts CA83(2): 12838p.
Chemical Abstracts CA82(15): 97460d.
Chemical Abstracts CA81(1): 3281a.
Chemical Abstracts CA76(21): 126097z.
Chemical Abstracts CA74(9): 41808r.
Chemical Abstracts CA68(2): 6886u.

*Primary Examiner*—John S. Maples
*Assistant Examiner*—Chhaya Sayala
*Attorney, Agent, or Firm*—Donald R. Cassady; Richard S. Roberts

[57] ABSTRACT

The invention provides a process for the production of $C_1$ to $C_5$ alkyl nitrite by forming an aqueous solution of $C_1$ to $C_5$ alkyl alcohol an alkali metal nitrite; cooling it; then slowly adding a hydrohalic acid solution while it is stirring; the reaction temperature is maintained in the range of from about $-10°$ C. to about $10°$ C. until the reaction is substantially complete; and the two formed phases are separated in a separatory funnel.

18 Claims, No Drawings

METHOD FOR PRODUCING C₁ TO C₅ ALKYL NITRIDES

BACKGROUND OF THE INVENTION

The present invention relates to the production of $C_1$ to $C_5$ alkyl nitrites and most particularly to an improved method for the production of isopropyl nitrite. Isopropyl nitrite is known per se and finds use as an intermediate in the production of the biocide Paraclox which is alpha-chloro-alpha-oximino-4-hydroxyacetophenone. This latter compound has the structural formula

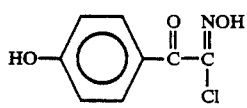

The preparation of this compound has been described by N. Levin and W. H. Hartong, *Journal of Organic Chemistry*, (1942), 7,408. Preparation proceeds by reacting hydroxyphenacyl chloride with isopropyl nitrite in the presence of hydrogen chloride to yield the product. The reaction can be depicted by:

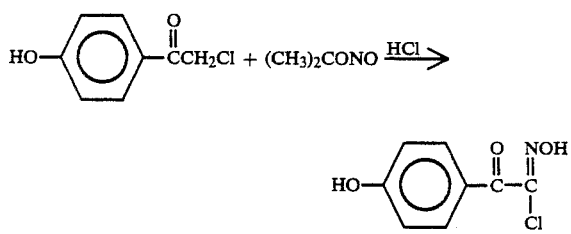

Alpha-chloro-alpha-oximino-4-hydroxyacetophenone is known to have good antibacterial and germicidal properties. Thus, the compound has found use as an industrial biocide to control the growth of bacteria and microorganisms which develop in water-based media used in the manufacture of various industrial products. Its antibacterial and germicidal properties are more fully described in U.K. Pat. No. 1,290,646.

The preparation of isopropyl nitrite is known in the art. Organic Synthesis Coll. Vol 3, 191 (1955) at pages 26–27 teaches the formation of a water, isopropanol, sulfuric acid mixture which is then added to an aqueous sodium nitrite solution. A problem with this method is the formation of a three phase reaction product including solid sodium sulfate in a third phase. In this prior art method, the isopropanol and sulfuric acid are first premixed and then dripped into sodium nitrite. The same problem is noted in the production of n-butyl nitrite at Organic Syntheses Coll. Vol 2, 108 (1943) at page 108. It has now been found that $C_1$ to $C_5$ alkyl nitrites may be prepared by a one step reaction of a $C_1$ to $C_5$ alkyl alcohol, an alkali metal nitrite and a hydrohalic acid in aqueous media. In the most preferred embodiment one may produce isopropyl nitrite by reacting isopropanol with sodium nitrite and hydrochloric acid in water according to the scheme:

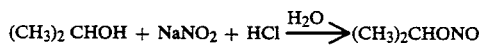

It has been unexpectedly found that by premixing the isopropanol and sodium nitrite and then adding the hydrochloric acid, that there is a decreased production of the nucleophilic substitution product, such as isopropyl chloride, as an impurity. The result is a two phase reaction product, a lower aqueous phase which is a saturated sodium chloride solution and an upper organic phase of isopropyl nitrite. These phases are then separated easily.

SUMMARY OF THE INVENTION

The invention provides a process for the production of $C_1$ to $C_5$ alkyl nitrites which comprises forming and continuously stirring an aqueous solution of a $C_1$ to $C_5$ alkyl alcohol and an alkali metal nitrite, cooling the solution to a temperature in the range of from about $-10°$ C. to about $10°$ C.; then slowly adding a hydrohalic acid which is maintained at a temperature range of from about $-10°$ C. to about $30°$ C., to said stirring solution while maintaining a reaction temperature in the range of from about $-10°$ C. to about $10°$ C. until the reaction is substantially complete; and separating the formed phases.

DETAILED DESCRIPTION OF THE PREFERRED EMBODIMENT

As hereinbefore mentioned, the invention produces $C_1$ to $C_5$ alkyl nitrites, most particularly isopropyl nitrite. Isopropyl nitrite may be prepared by reacting an aqueous solution of isopropyl alcohol, and an alkali metal nitrite to which is added a hydrohalic acid while the exothermic reaction is cooled.

In the most preferred embodiment, the $C_1$ to $C_5$ alkyl alcohol is isopropyl alcohol, or t-butyl alcohol, the alkali metal nitrite is sodium nitrite and the hydrohalic acid is hydrochloric acid. The preferred embodiment will be more fully set forth, however, the other variations may be produced analogously. As an important feature of the invention, one first premixes an aqueous solution of $C_1$ to $C_5$ alcohol and alkali metal nitrite. The mixture is continuously stirred and cooled at a temperature of from about $-10°$ C. to about $10°$ C., or more preferably from about $-5°$ C. to about $5°$ C. The amount of $C_1$ to $C_5$ alkyl alcohol preferably ranges from about 1.0 moles to about 0.80 moles, or more preferably from about 1.0 moles to about 0.9 moles, based on the number of moles alkali metal nitrite. In the preferred embodiment the amount of alkali metal nitrite range from about 1.0 mole to about 1.2 moles or more preferably from about 1.0 mole to about 1.07 moles, based on the number of moles of alcohol.

In the preferred embodiment the water is present in sufficient amount to form a solution of the alcohol and the alkali metal nitrite. In the preferred embodiment this may range from about 80 to about 40 weight percent based on the combined weight of alcohol, water and alkali metal nitrite. In the most preferred case, water is introduced only in the amount realized from the use of commercially available (ca. 40%) sodium nitrite solution. Once this pre-formed solution is made, cooled, and stirring, one adds the hydrohalic acid to the solution in a dropwise fashion. The preferred acid is commercially available concentrated, aqueous (ca. 85%) HCl but HF, HBr and HI can be used also. The amount of acid added may range from about 1.0 mole to about 0.9 mole and preferably from about 1.0 mole to about 0.95 mole based on the moles of sodium nitrite. Prior to the acid addition it is first cooled to from about $-10°$ C. to about $30°$ C. or preferably about $-10°$ C. to about $10°$ C. and most preferably about −5° C. to about 5° C. The overall mixture is also held to this temperature during the entire reaction. The acid is added to the solution slowly over a period of from about 1 to about 8 hours or more preferably from about 1 to about 4 hours. The reaction mixture is a two liquid phase reaction product which is separated in a separatory funnel. The lower phase is discarded aqueous sodium chloride. In the preferred embodiment, the molar ratio of hydrohalic acid to alcohol ranges from about 1.0 to 1.1. In the preferred embodiment the molar ratio of alkali metal nitrite to hydrohalic acid ranges from about 1.0 to about 1.1. A most preferred molar ratio of alcohol to hydrohalic acid to alkali metal nitrite is about 1.0:1.04:1.07. The upper phase contains the $C_1$ to $C_5$ alkyl nitrite at a purity of over 90% and usually over 97%. The following non-limiting examples serve to illustrate the invention.

EXAMPLE 1

Comparative Example

A three neck 3 liter round bottom flask is equipped with an overhead stirrer, a refrigerated water jacketed addition funnel, and a thermowell. The flask is charged with 227.7 g of sodium nitrite and 1 liter of water. The contents are then stirred and cooled with an ice/acetone bath to 0° C. Next, water (60 ml), isopropyl alcohol (230 ml), and concentrated sulfuric acid (80 ml) are mixed in a beaker and cooled to 8° C. This mixture is then placed in the addition funnel and added slowly (ca. 4.5 hrs.) to the stirred flask under the liquid level while holding the temperature of the flask between −3° C. and +1° C. The stirrer is stopped and the contents of the flask poured into a 2 liter beaker which is placed in an ice bath. The phases are allowed to separate and then the aqueous and organic phases decanted (from the solids) into a separatory funnel where the aqueous phase is removed. The organic phase is then washed with 2-60 ml portions of an aqueous solution prepared by dissolving 2 g $NaHCO_3$ and 25 g NaCl in 120 ml of water. The organic phase (isopropyl nitrite, 136 g) is stored over anhydrous $K_2CO_3$ in the refrigerator.

EXAMPLE 2

A three neck 2 liter round bottom flask is equipped with an overhead stirrer, a thermowell, and a refrigerated water jacketed addition funnel. The flask is charged with 228 g sodium nitrite, 350 ml water, and 230 ml isopropanol. The contents are stirred and cooled with an ice/acetone bath to −5° C. Then 260 ml of concentrated hydrochloric acid is cooled to 0° C. and placed in the addition funnel. The HCl is added to the stirred flask slowly over a 4 hour period while keeping the temperature between −5° C. and 0° C. The two phase solution is allowed to stir for 30 minutes and then poured into a separatory funnel. The phases are separated and the organic phase (isopropyl nitrite, 264 g) stored in the refrigerator.

EXAMPLE 3

A three neck 2 liter round bottom flask is equipped with an overhead stirrer, a thermowell, and an addition funnel. The flask is charged with 228 g sodium nitrite, 350 ml water, and 230 ml isopropanol. The contents are stirred and cooled with an ice/acetone bath to −5° C. Then 260 ml of concentrated hydrochloric acid is cooled to 0° C. and placed in the addition funnel. The HCl is added to the stirred flask slowly over a ca. 4 hour period while keeping the temperature below 5° C. The two phase solution is allowed to stir for 30 minutes at 0° C. and then poured into a separatory funnel. The phases are separated and the organic phase (isopropyl nitrite, 261 g) stored in the refrigerator.

EXAMPLE 4

A three neck 2 liter round bottom flask is equipped with a magnetic stirrer, a thermowell, and a refrigerated water jacketed addition funnel. The flask is charged with 228 g sodium nitrite and 350 ml water. The contents are stirred and cooled with an ice/acetone bath to −5° C. Then 260 ml of concentrated hydrochloric acid and 230 ml isopropanol are mixed and cooled to 5° C. and placed in the addition funnel. The HCl/isopropanol mixture is added to the stirred flask slowly over a 2 hour period while keeping the temperature below 0° C. The two phase solution is allowed to stir for 15 minutes and then poured into a separatory funnel. The phases are separated and the organic phase (isopropyl nitrite, 248 g) stored in the refrigerator.

EXAMPLE 5

A three neck 2 liter round bottom flask is equipped with a magnetic stirrer, a thermowell, and two addition funnels. The flask is charged with 228 g sodium nitrite and 500 ml water. The contents are stirred and cooled with an ice/acetone bath to 0° C. Then 250 ml of concentrated hydrochloric acid is cooled 0° C. and placed in one of the addition funnels and 282 ml t-butanol placed in the other addition funnel. The HCl and the t-butanol are added to the stirred flask slowly over a 1 hour period while keeping the temperature below 0° C. The two phase solution is allowed to stir for 1 hour and then poured into a separatory funnel. The phases are separated and the organic phase (t-butyl nitrite, 247 g) stored in the refrigerator.

EXAMPLE 6

A three neck 2 liter round bottom flask is equipped with a magnetic stirrer, a thermowell, and an addition funnel. The flask is charged with 228 g sodium nitrite, 350 ml water and 282 ml t-butanol. The contents are stirred and cooled with an ice bath to 0° C. Then 260 ml of concentrated hydrochloric acid is placed in the addition funnel and added to the stirred flask slowly over a 4 hour period while keeping the temperature below 5° C. The two phase solution is allowed to stir for 30 minutes and then poured into a separatory funnel. The phases are separated and the organic phase (t-butyl nitrite, 300 g) stored in the refrigerator.

What is claimed is:

1. A process for the production of $C_1$ to $C_5$ alkyl nitrite which comprises forming and continuously stirring an aqueous solution of a $C_1$ to $C_5$ alkyl alcohol and an alkali metal nitrite, cooling the solution to a temperature in the range of from about −10° C. to about 10° C.; then slowly adding a hydrohalic acid which is maintained at a temperature range of from about −10° C. to about 30° C., to said stirring solution while maintaining a reaction temperature in the range of from about −10° C. to about 10° C. until the reaction is substantially complete; and separating the formed phases.

2. The process of claim 1 wherein said temperatures range from about −5° C. to about 5° C.

3. The process of claim 1 wherein the reaction is conducted for from about 1 to about 8 hours.

4. The process of claim 1 wherein the reaction is conducted for from about 1 to about 4 hours.

5. The process of claim 1 wherein the alkali metal nitrite is sodium nitrite or potassium nitrite.

6. The process of claim 1 wherein the alcohol is isopropanol or t-butyl alcohol.

7. The process of claim 1 wherein the hydrohalic acid is selected from the group consisting of HCl, HBr, HF and HI.

8. The process of claim 1 wherein the hydrohalic acid is HCl.

9. The process of claim 1 wherein the molar ratio of hydrohalic acid to alcohol ranges from 1.0 to about 1.1.

10. The process of claim 1 wherein the molar ratio of alkali metal nitrite to hydrohalic acid ranges from about 1.0 to about 1.1.

11. The process of claim 1 wherein the molar ratio of alcohol to hydrohalic acid to alkali metal nitrite is about 1.0:1.04:1.07.

12. The process of claim 1 wherein the hydrohalic acid is hydrochloric acid, the alcohol is isopropyl alcohol or t-butyl alcohol and the alkali metal nitrite is sodium nitrite.

13. The process of claim 12 wherein the molar ratio of hydrochloric acid to alcohol ranges from 1.0 to about 1.1.

14. The process of claim 12 wherein the molar ratio of sodium nitrite to hydrochloric acid ranges from about 1.0 to about 1.1.

15. The process of claim 12 wherein the molar ratio of alcohol to hydrochloric acid to sodium nitrite is about 1.0:1.04:1.07.

16. The process of claim 12 wherein said temperatures range from about $-5°$ C. to about $5°$ C.

17. The process of claim 12 wherein the reaction is conducted for from about 1 to about 8 hours.

18. The process of claim 12 wherein the reaction is conducted for from about 1 to about 4 hours.

* * * * *

UNITED STATES PATENT AND TRADEMARK OFFICE
CERTIFICATE OF CORRECTION

PATENT NO.    :   4,980,496
DATED         :   December 25, 1990
INVENTOR(S)   :   Olan Stanley Fruchey It is certified that error appears in the above—identified patent and that said Letters Patent is hereby corrected as shown below:

On the title page and col. 1-2 should read:

METHOD FOR PRODUCING $C_1$ TO $C_5$ ALKYL NITRITES

Title page, the following Assignee should be present:

[73] Assignee:   HOECHST CELANESE CORPORATION
                 Somerville, New Jersey Signed and Sealed this First Day of December, 1992

*Attest:*

DOUGLAS B. COMER

*Attesting Officer*     *Acting Commissioner of Patents and Trademarks*